(12) United States Patent
Fukukita et al.

(10) Patent No.: US 6,344,023 B1
(45) Date of Patent: Feb. 5, 2002

(54) ULTRASONIC DIAGNOSTIC IMAGING SYSTEM

(75) Inventors: Hiroshi Fukukita, Tokyo; Morio Nishigaki, Fujisawa; Takao Suzuki, Yokohama, all of (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/699,458

(22) Filed: Oct. 31, 2000

(30) Foreign Application Priority Data

Nov. 1, 1999  (JP) .......................................... 11-311139

(51) Int. Cl.[7] ................................................. A61B 8/00
(52) U.S. Cl. ........................ 600/443; 600/447; 600/441
(58) Field of Search ................................ 600/443, 447, 600/444, 448, 449, 437, 441, 440

(56) References Cited

U.S. PATENT DOCUMENTS

| 4,368,643 A |   | 1/1983 | Tachita et al. ............... 73/626 |
| 5,577,505 A |   | 11/1996 | Brock-Fisher et al. . 128/662.02 |
| 6,102,859 A | * | 8/2000 | Mo ............................. 600/443 |
| 6,228,031 B1 | * | 5/2001 | Hwang et al. ............... 600/447 |
| 6,251,074 B1 | * | 6/2001 | Averkiou et al. ............ 600/447 |
| 6,283,919 B1 | * | 9/2001 | Roundhill et al. ........... 600/447 |

FOREIGN PATENT DOCUMENTS

WO    WO 98/20362    5/1998

OTHER PUBLICATIONS

European Patent Office Search Report dated Feb. 28, 2001.

* cited by examiner

Primary Examiner—Marvin M. Lateef
Assistant Examiner—Maulin Patel
(74) Attorney, Agent, or Firm—McDermott, Will & Emery

(57) ABSTRACT

A nonlinear distortion-based ultrasonic diagnostic imaging system displays a raised-resolution video of tissue inside a body at an increased frame rate. Using a two-pulse technique, a transducer driver supplies narrower-width and wider-width driving pulses to a transducer, which transmits weaker and stronger ultrasonic wave pulses alternately while putting the same intervals between adjacent ultrasonic wave pulses to obtain a weaker echo and a stronger echo. An equalizer equalizes each weaker echo to the stronger echo into an equalized weaker echo. An interpolator calculates an interpolation value between the equalized weaker echo and an equalized previous weaker echo obtained from a previous weaker echo. For each weaker ultrasonic wave pulse, a detector finds a difference between the interpolation value and a stronger echo obtained between the weaker echo and the previous weaker echo. The equalization and interpolation enables high-speed scanning, which has not been achieved with two-pulse technique. Thus, a raised-resolution video signal of the tissue is formed at an increased frame rate on the basis of the difference signal and a scan control signal which is also used in the transducer.

12 Claims, 4 Drawing Sheets

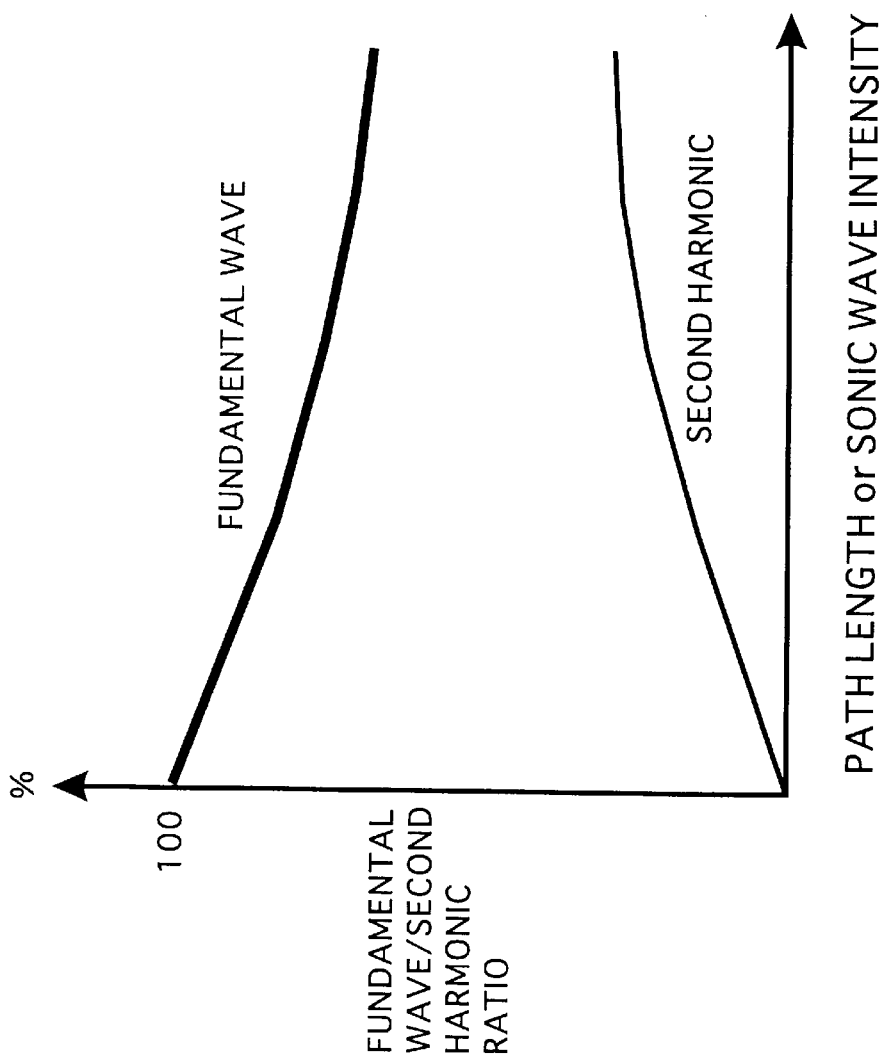
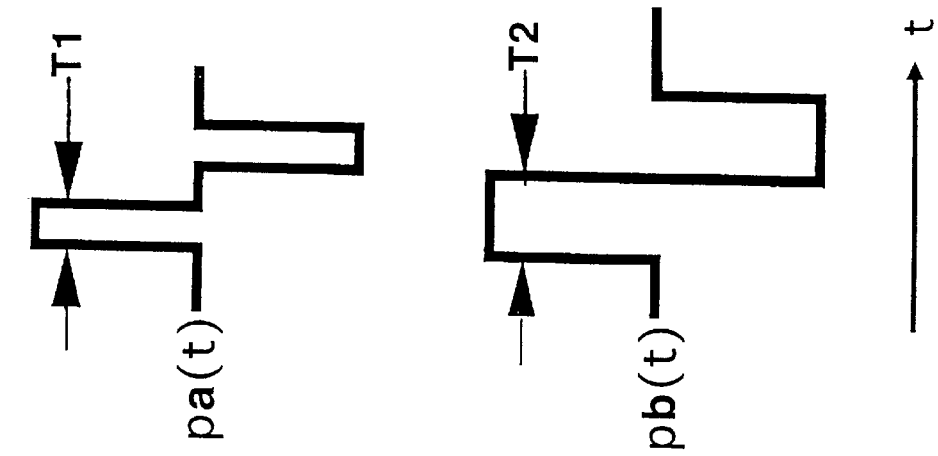

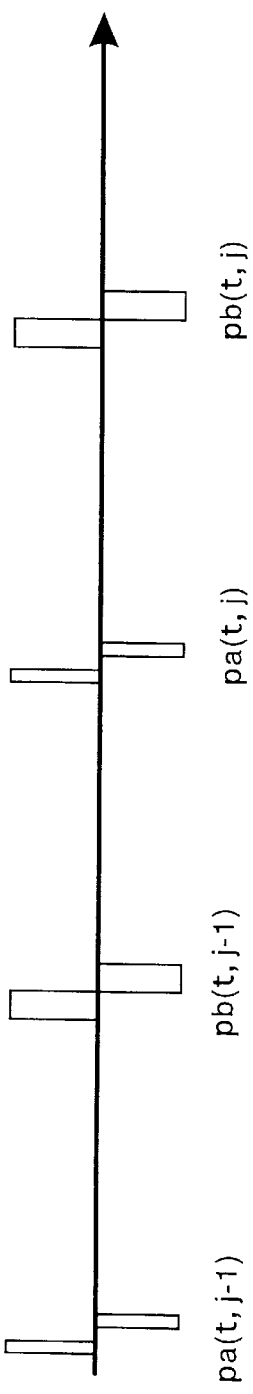
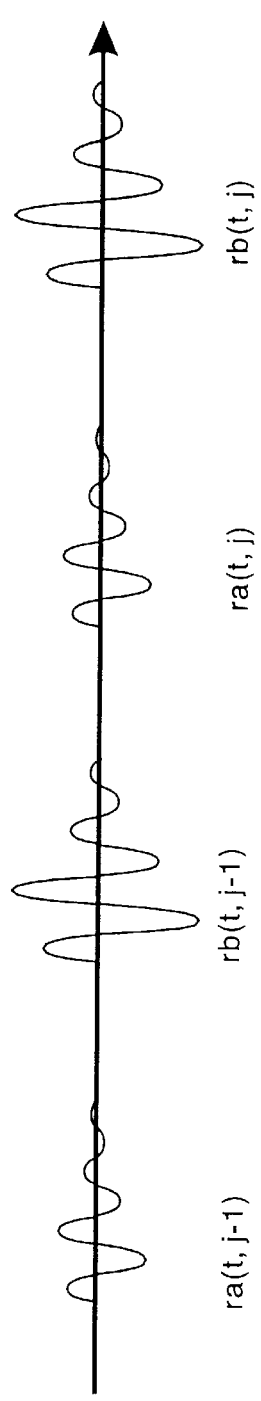
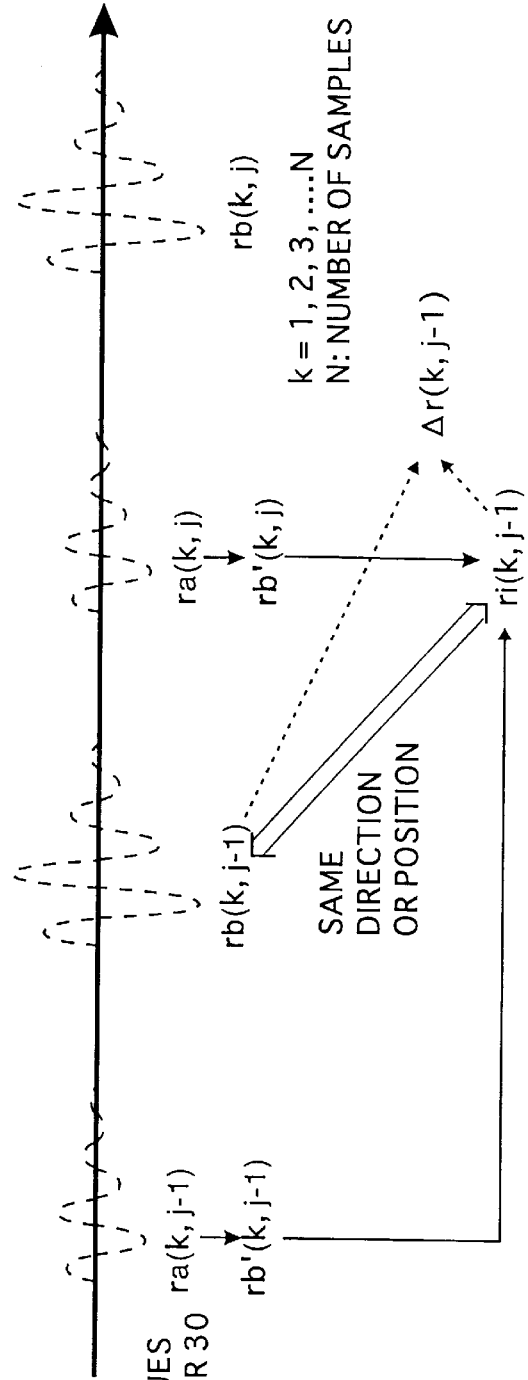
FIG. 5A DRIVING PULSES SUPPLIED TO THE TRANSDUCER
FIG. 5B ULTRASONIC ECHO
FIG. 5C WAVEFORM DEFINED BY THE OUTPUT VALUES FROM A/D CONVERTER 30

ULTRASONIC DIAGNOSTIC IMAGING SYSTEM

BACKGROUND OF THE INVENTION

1. Field of the Invention

The invention relates to an ultrasonic diagnostic imaging system that uses nonlinear distortion for imaging tissue inside a body.

2. Description of the Prior Art

Ultrasonic diagnostic imaging systems for imaging tissue inside a body by utilizing nonlinear propagation distortion caused by harmonics occurring during ultrasonic wave propagation are well known in the art. In such a system, a transducer is driven alternately by a first and a second drive pulse of A and 2A, respectively, in amplitude. The transducer responsively transmits a first and a second ultrasonic wave, which are reflected by tissue in the body and received by the transducer as a first and a second ultrasonic echo of B and 2B, respectively, in amplitude. The first and second echoes are amplified by a variable gain amplifier with gains of C and C/2 to yield a first and a second signal of B·C and 2B·(C/2), respectively. Since the sidelobes of the first and second echoes are much smaller than the main lobes and accordingly small in distortion, the amplitudes of the sidelobes of the second echo are substantially twice those of the sidelobes of the first echo. Thus calculating the differences between the first and second signals, i.e., B·C–2B·(C/2) enables the detection of the depth of reflection point. Since a pair of pulses is used for each analysis, such systems as described above are called "two-pulse" systems. A first and a second pulse in such a two-pulse system are hereinafter referred to as a "former pulse" and a "latter pulse".

However, in order for the above imaging technique to work satisfactorily, the reflection points or ultrasonic wave transmission directions from which the former and later echoes are obtained must be substantially the same. This restriction prevents high-speed scanning in conventional nonlinear distortion-based ultrasonic diagnostic imaging system.

SUMMARY OF THE INVENTION

In light of the above, it is an object of the present invention to provide a nonlinear distortion-based ultrasonic diagnostic imaging system which displays a raised-resolution video of tissue inside a body at an increased frame rate.

According to an aspect of the invention, a transducer transmits a ultrasonic wave pulse in response to a driving pulse while scanning the transmission direction in response to a scan control signal and receives an echo of the ultrasonic wave pulse to provide an echo signal. A transducer driver supplies the driving pulses and the scan control signal to the transducer such that the transducer transmits weaker and stronger ultrasonic wave pulses alternately while putting the same intervals between adjacent ultrasonic wave pulses to obtain a weaker echo of the weaker ultrasonic wave pulse and a stronger echo of the stronger ultrasonic wave pulse from the transducer. An equalizer equalizes each weaker echo to the stronger echo into an equalized weaker echo. An interpolator calculates an interpolation value between the equalized weaker echo and an equalized previous weaker echo obtained from a previous weaker echo. For each weaker ultrasonic wave pulse, a detector finds a value indicative of a difference between the interpolation value and a stronger echo obtained between the weaker echo and the previous weaker echo. An image processor generates a raised-resolution video signal of the tissue at an increased frame rate on the basis of the values and the scan control signal.

In one embodiment, the equalizer calculates a convolution by using each weaker echo as one of two components.

In the embodiment, the transducer driver may supply a narrower driving pulse and a wider driving pulse for the weaker and stronger ultrasonic wave pulses, respectively. Alternatively, the transducer driver may supply fewer driving pulse(s) for the weaker ultrasonic wave pulse and supply more driving pulses for the stronger ultrasonic wave pulse. These driving pulses have an identical width.

In the embodiment, the interpolator calculates an arithmetic means of said equalized weaker echo and said equalized previous weaker echo. Alternatively, an arithmetic means of the absolute values of the equalized weaker echo and the equalized previous weaker echo may be calculated.

BRIEF DESCRIPTION OF THE DRAWING

The features and advantages of the present invention will be apparent from the following description of an exemplary embodiment of the invention and the accompanying drawings, in which:

FIG. 2 is a diagram showing waveforms of driving pulses with respective different pulse widths T1 and T2;

FIG. 3 is a graph showing the relationship between the fundamental wave and the second harmonic of an ultrasonic echo;

FIG. 5 is a diagram showing various signals for illustrating the operation of the ultrasonic diagnostic imaging system of FIG. 1

Throughout the drawing, the same elements when shown in more than one figure are designated by the same reference numerals.

DETAILED DESCRIPTION OF THE PREFERRED EMBODIMENTS

Figure 1:
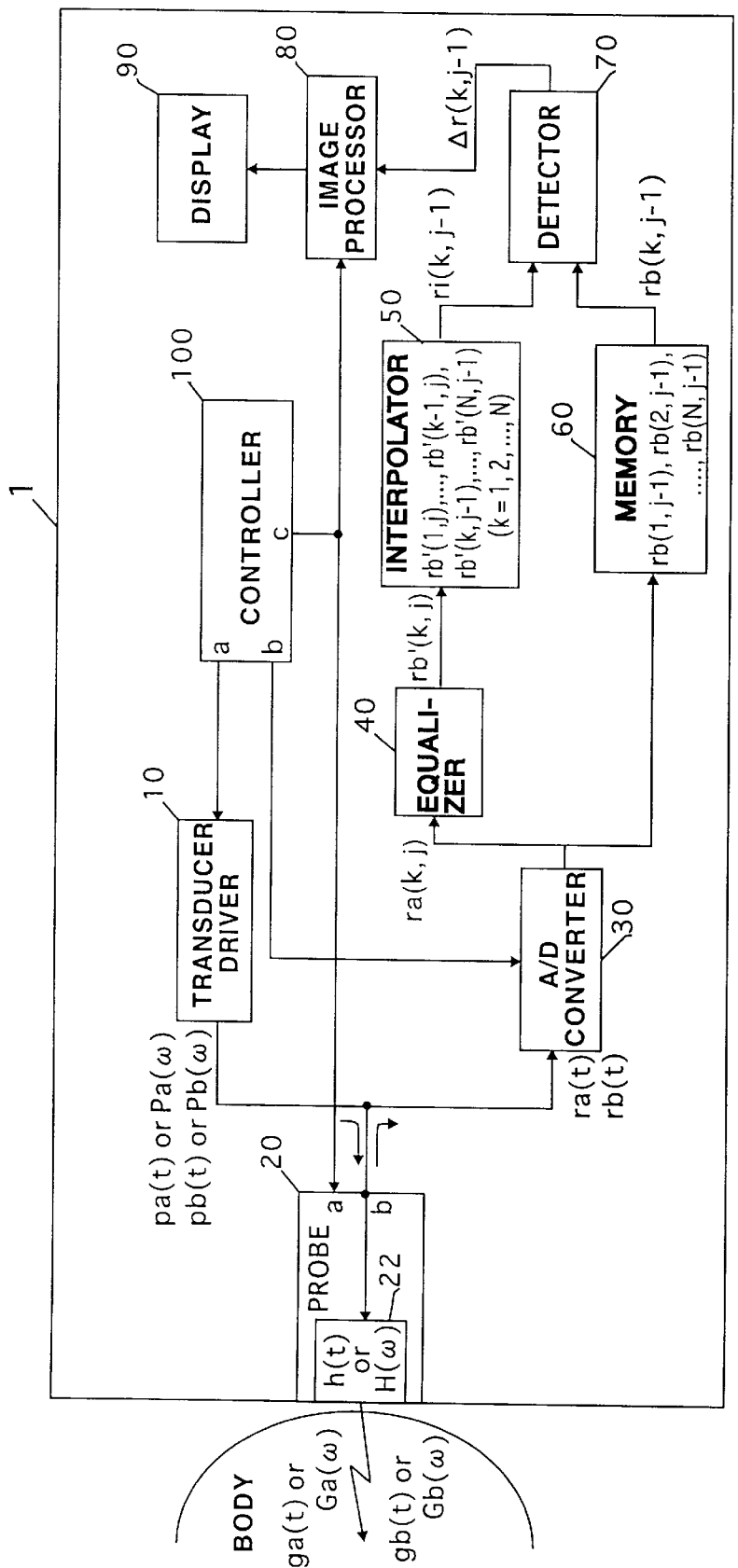
FIG. 1 is a schematic block diagram showing an arrangement of an ultrasonic diagnostic imaging system according to an illustrative embodiment of the invention.
Figure 4:
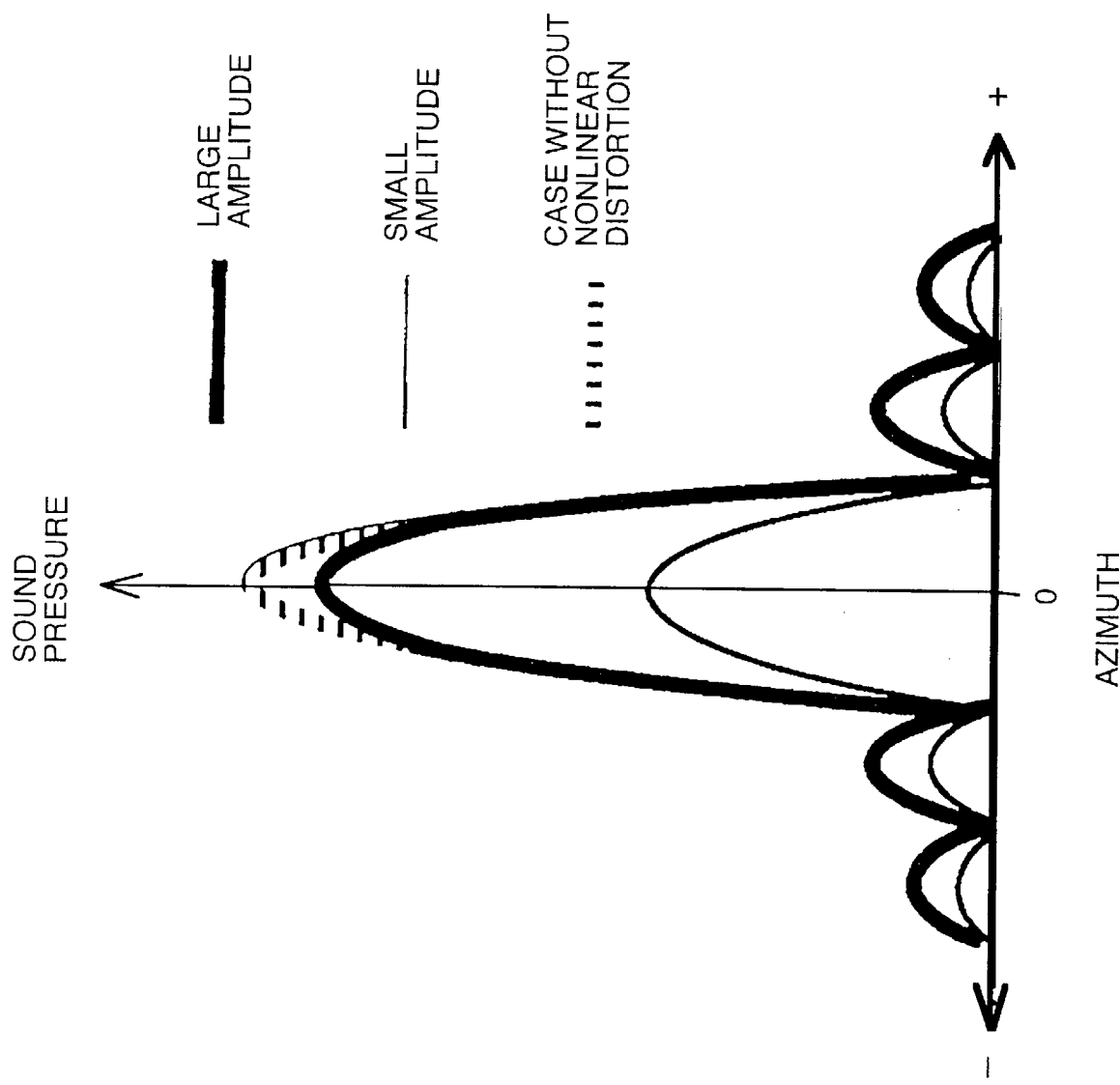
FIG. 4 is a diagram showing the relationship between the azimuth (i.e., the angle with a normal on the transmission surface of transducer 22) and the amplitude of the transmitted ultrasonic wave.

FIG. 1 is a schematic block diagram showing an arrangement of an ultrasonic diagnostic imaging system according to an illustrative embodiment of the invention. In FIG. 1 the ultrasonic diagnostic imaging system 1 comprises a transducer driver 10 for alternately providing a former and a latter driving pulse different from each other in spectral intensity and a probe 20, which includes a transducer 22 for transmitting a ultrasonic wave pulse in response to a driving pulse and receiving an echo of the transmitted ultrasonic wave pulse. The probe 20 has its scan data input 20a connected to the controller scan control output 100c and its transducer terminal 20b connected to the transducer driver 10 output. The system 1 further comprises an analog-to-digital (A/D) converter 30 having its analog input connected to the transducer terminal 20b and its control input connected to the controller output 100b; an equalizer 40 having its input connected to the output of the A/D converter 30; an interpolator 50 having its input connected to the equalizer 40 output; a memory 60 for temporary storing one pulse's worth of digital echo samples from the A/D converter 30; a detector 70 which uses the interpolator 50 output and the A/D converter 30 output being temporarily stored in the memory 60 to detect a signal indicative of the depth of reflection point; an image processor 80 having its data input connected to the detector 70 output and its control input connected to the controller output 100c; a display device 90 having its input connected to the image processor 80; and a controller 100 which controls the operation of the whole system 1 especially by providing control signals 100a through 100c.

Since the driving pulses from the transducer driver 10 typically have a high voltage, the A/D converter 30 is preferably provided with a limiter (not shown). The interpolator 50 is preferably provided with a not-shown memory (or interpolator memory) with a capacity enough to store one pulse's worth of equalized digital echo samples from the equalizer 40. The memory 60, which is shown as an independent memory in FIG. 1, may be a part of random access memory (not shown) included in the controller 100. The controller 100 may be any suitable microprocessor-based controller.

In operation, the transducer driver 10 alternately outputs a former and a latter driving pulse different from each other in duty cycle in response to a transmission control signal from the controller 100 output terminal 100a as shown in FIG. 5A. FIG. 2 shows the former driving pulse pa(t) and the latter driving pulse pb(t), which means that the former and latter driving pulses are expressed by respective functions of time t, i.e., pa(t) and pb(t). The pulses preferably have three values, i.e., 0 and positive and negative levels of a predetermined amplitude. The pulses have respective pulse widths T1 and T2. FIG. 5 shows various signals for illustrating the operation of the ultrasonic diagnostic imaging system 1 of FIG. 1. In FIG. 5, a letter "j" is used to indicate the sequence of pulses (i.e., "j" is a serial number assigned to each pair of a former and a latter pulse in order of generation). For example, in FIG. 5A, the current former driving pulse is denoted by pa(t, j) and the previous former driving pulse is denoted by pa(t, j−1). In the same way, ultrasonic echoes of the ultrasonic wave pulses transmitted in response to the driving pulses pa(t, j) and pa(t, j−1) are denoted by ra(r, j) and ra(t, j−1), respectively. However, if there is no need of differentiating the sequence of the pulses, we will use simplified expressions like pa(t), ra(t), etc., omitting the sequence ID terms in the following.

The transducer 22 alternately transmits former ultrasonic waves ga(t) and latter ultrasonic waves gb(t) that are in a fundamental frequency band and correspond to the former pa(t) and latter pb(t) driving pulses. Preferably, the probe 20 is so arranged as to automatically scan the direction of ultrasonic wave transmission in response to the scan control data from the controller output 100c. Since the transducer 22 has a narrower frequency band width as compared with the driving pulses, changing the spectral intensity of the driving pulse (i.e., changing the pulse width of the driving pulse with its amplitude kept constant) enables the control of the amplitude of the transmitted ultrasonic waves. For this reason, the former pa(t) and latter pb(t) driving pulses with respective pulse widths of T1 and T2 cause the transducer 22 to transmit the former ga(t) and latter gb(t) ultrasonic waves of respective amplitudes responsive to T1 and T2.

FIG. 3 shows the relationship between the fundamental wave and the latter harmonic in an echo of a transmitted ultrasonic wave pulse. As seen from FIG. 3, the ultrasonic wave pulses ga(t) and gb(t) transmitted from the transducer 22 increase in nonlinear distortion as they travel a longer path within the body. The larger the amplitude of the ultrasonic waves is, the harder the nonlinear distortion is. Since the nonlinear distortion is due to harmonics, especially, due to the latter harmonic, the fundamental wave component decreases in amplitude as the latter harmonic increases. For this reason, the peak portion of the main lobe, in which the amplitude of the beam of ultrasonic wave pulse is relatively large, is subjected to larger nonlinear distortion, while the sidelobes, in which the amplitude is relative small, are subjected to smaller nonlinear distortion.

The former ga(t, j) and latter gb(t, j) ultrasonic wave pulses transmitted from transducer 22 in response to the driving pulses pa(t, j) and pb(t) is reflected by tissue within the body, and returned to and received by transducer 22 as a former and a latter ultrasonic echo ra(t, j) and rb(t, j), respectively, as shown in FIG. 5B. Each of former ra(t, j) and latter rb(t, j) echo pulses is sampled and converted by A/D converter 30 into a series of digital echo samples (or signals), ra(k, j) and rb(k, j), as shown in FIG. 5C, where k=1, 2, . . . , N, where N is the number of digital echo samples for one driving or echo pulse.

In order to facilitate the understanding of the invention, it is now assumed that the transducer driver 10 has just supplied a j-th former driving pulse pa(t, j) and, accordingly, now is just the time to analyze echo pulses ra(t, j−1), rb(t, j−1) and ra(t, j) to get the j−1)th result. At the time of transmission of a j-th former ultrasonic wave pulse ga(t, j) from the transducer 22, the digital samples of the j−1)th former echo pulse, i.e., ra(1, j−1), ra(2, j−1), . . . , ra(N, j−1) (hereinafter, denoted as {ra(k, j−1)|k=1~N}) have been stored in memory of either interpolator 50 or controller 100 (not shown), and the digital samples of the j−1)th latter echo pulse, i.e., rb(1, j−1), rb(2, j−1), . . . , rb(N, j−1) (hereinafter, denoted as {rb(k, j−1)|k=1~N}) have been stored in memory 60 as shown in FIG. 1. Then, each of the digital samples of the j-th former echo pulse ra(t, j) which are supplied from A/D converter 30 is processed on a sample by sample basis. In the following, we will discuss how the k-th sample ra(k, j) of the j-th former echo pulse ra(t, j) is processed along the circuit path following A/D converter 30.

Specifically, the k-th former echo digital sample ra(k, j) is equalized by equalizer 40 into an equalized digital sample rb'(k, j) as detailed later. Interpolator 50 uses the just equalized signal rb'(k, j) for interpolation together with the corresponding one rb'(k, j−1) of the equalized digital samples of the preceding former echo rb'(1, j−1), rb'(2, j−1), . . . , rb'(N, j−1). For this purpose, interpolator 50 preferably retains the recent N equalized samples:

rb'(k, j−1), rb'(k+1, j−1), . . . , rb'(N, j−1), rb'(1, j), rb'(2, j), . . . , rb'(k−1, j).

Then, interpolator 50 has only to use the just equalized signal rb'(k, j) and the oldest one of the stored signals, rb'(k, j−1) to calculate and output an interpolation value si(k, j−1).

It is noted that as shown in FIG. 1 the recent N equalized samples are actually stored in the following order:

rb'(1, j), rb'(2, j), . . . , rb'(k−1, j), rb'(k, j−1), rb'(k+1, j−1), . . . , rb'(N, j−1). (data 1)

This is because, on completing the calculation of interpolation value si(k, j−1), interpolator 50 writes the newest (or just used) equalized sample rb'(k, j) over the oldest (or just used) one rb'(k, j−1) of the equalized digital samples (data 1) stored in the interpolation 50 memory.

The detector 70 calculates the difference between the interpolator 50 output ri(k, j−1) and the corresponding one rb(k, j−1) of the digital samples of the preceding (i.e., j−1)th) latter which are stored in memory 60 as follows:

$$\Delta r(k, j-1) = ri(k, j-1) - rb(k, j-1).$$

The image processor 80 processes thus obtained differences $\Delta r(k, j-1)$ for k=1~N for each of j=1, 2, . . . together with the scan data from the controller output terminal 100c to provide video images of tissue inside the body. The video images are displayed on the display device 90.

The principles of the invention, especially, the operation of equalizer 40 and interpolator 50 will be detailed in the following. The Fourier transforms for a former pa(t) and a latter pb(t) driving pulse are denoted by Pa($\omega$) and Pb($\omega$), where $\omega$ is the angular frequency of the former and latter driving pulses. Similarly, the Fourier transforms for a former ga(t) and a latter gb(t) ultrasonic wave pulse are denoted by Ga($\omega$) and Gb($\omega$). Also, assuming the impulse response of the transducer 22 to be h(t), then the Fourier transform for the impulse response h(t) is denoted by H($\omega$).

Then, since a transmitted ultrasonic wave pulse ga(t) is expressed by the convolution of the impulse response h(t) and the driving pulse pa(t), it follows:

$$ga(t) = h(t) * pa(t) \qquad (1)$$

where X*Y indicates the convolution of X and Y. This means $$Ga(\omega) = H(\omega) \times Pa(\omega). \qquad (2)$$

Multiplying the both sides of equation (2) by Pb($\omega$)/Pa($\omega$), we obtain $$Ga(\omega) \times (Pb(\omega)/Pa(\omega)) = H(\omega) \times Pa(\omega) \times (Pb(\omega)/Pa(\omega)) \qquad (3)$$
$$= H(\omega) \times Pb(\omega)$$
$$= Gb(\omega).$$

Expressing the equation (3) in the time domain yields $$gb(t) = ga(t) * invf(Pb(\omega)/Pa(\omega)) \qquad (4)$$

where the function invf(F($\omega$)) indicates the inverse Fourier transform for the function F($\omega$). The equation means that calculating the convolution between the former ultrasonic wave function ga(t) of the time when transducer 22 is a driven by a driving pulse pa(t) and the function invf(Pb($\omega$)/Pa($\omega$)) yields the latter ultrasonic wave function gb(t) of the time when transducer 22 is driven by a driving pulse pb(t).

Assuming that a returned echo of a transmitted ultrasonic wave is expressed by a linear combination of the transmitted ultrasonic wave, then the equation (4) can be written, for j-th former and latter echoes, as:

$$rb(t, j) = ra(t, j) * invf(Pb(\omega, j)/Pa(\omega, j)). \qquad (5)$$

From this equation, it is seen that if equalizer 40 calculates the convolution of a j-th former echo ra(t, j) and the function invf(Pb($\omega$, j)/Pa($\omega$), j)), then equalizer 40 must provide a j-th latter echo rb(t, j). However, since the ultrasonic echoes ga(t) and gb(t) differ in amplitude, the nonlinear distortions in the ultrasonic echoes ga(t) and gb(t) also differ in degree. Taking this difference into account, the equation (5) should be written as:

$$rb(t, j) = ra(t, j) * invf(Pb(\omega, j)/Pa(\omega, j)) + \Delta r(t, j). \qquad (6)$$

Since the first term of the right side of equation (6) can be calculated by equalizer 40 as:

$$rb'(t, j) = ra(t, j) * invf(Pb(\omega, j)/Pa(\omega, j)). \qquad (7)$$

The calculation of equation (7) by equalizer 40 can be realized by, for example, a digital filter etc.

Using rb'(t, j) in equation (6) yields $$rb(t, j) = rb'(t, j) + \Delta r(t, j). \qquad (8)$$

Since the signals in a circuit path which follows A/D converter 30 are digital samples, equation (8) can be expressed as:

$$rb(k, j) = rb'(k, j) + \Delta r(k, j). \qquad (9)$$

However, since the scanning directions or positions (i.e., reflection points of transmitted latter gb(t) and former ga(t) ultrasonic wave pulses) that caused the ultrasonic echoes rb(t) and ra(t) (i.e., rb'(k, j)), respectively, are actually different from each other as seen from FIG. 5C, equation (9) is not valid as it is. In order to make the signals rb'(k, j) or ra(k, j) uniform in the scanning direction, the value rb'(k, j) is replaced, in interpolator 50, with:

$$ri(k, j) = \frac{rb'(k, j) + rb'(k, j+1)}{2}. \qquad (10)$$

By doing this, the difference $\Delta r(k, j)$ in equation (9) is given, in detector 70, by:

$$\Delta r(k, j) = rb(k, j) - ri(k, j). \qquad (11)$$

Considering that the pulse numbers j and j−1 indicate the current pulse and the preceding pulse, respectively, in actual operation, FIGS. 1 and 5C are drawn such that interpolator 50 calculates:

$$ri(k, j-1) = \frac{rb'(k, j-1) + rb'(k, j)}{2}, \text{ and} \qquad (10')$$

detector 70 calculates $$\Delta r(k, j-1) = rb(k, j-1) - ri(k, j-1). \qquad (11')$$

The difference ri(k, j) is regarded as a value caused by the peak portion of the main lobe in the latter or larger-amplitude ultrasonic echo rb(t, j) and indicates the depth of reflection point.

According to the present invention, as seen from FIG. 5C, the depth of reflection point (or tissue inside the body) in the scanning direction of a weaker and stronger ultrasonic wave pulse pair is detected by using three successive scanning points including one used for the preceding pair. Since such three successive scanning points are permitted to be specially apart from one other, this enables a high-speed scanning, i.e., displaying an increased number of frames per unit time, permitting the motion of tissue to be displayed smoothly.

However, it is noted that it is preferable to place the same intervals between adjacent driving signals.

Also, since the difference $\Delta r(k, j-1)$ includes substantially no sidelobe components, high-resolution images are obtained.

Modification

Interpolator 50 may calculate $$ri(k, j-1) = \frac{|rb'(k, j-1)| + |rb'(k, j)|}{2} \quad (12)$$

instead of equation (10').

Detector 70 may calculate $$\Delta r(k, j-1) = |rb(k, j-1)| - ri(k, j-1)| \quad (13)$$

instead of (11').

If equation (12) or (13) is used, then the use of absolute value eliminates phase components, causing only amplitude information to be used. This frees the difference $\Delta r(k, j-1)$ from becoming too large due to variation in phases of received echoes.

In the above illustrative embodiment, driving pulses of different pulse widths are used for driving pulse pairs. Pulse pairs may be realized by changing the number of pulses of a narrow pulse width.

A filter for compensating the spectral difference between the former and the latter driving pulses may be used for equalizer 40.

In the above illustrative embodiment, the weaker ultrasonic echoes have been equalized to the stronger ultrasonic echoes. Alternatively, the stronger ultrasonic echoes may be equalized to the weaker ultrasonic echoes.

Many widely different embodiments of the present invention may be constructed without departing from the spirit and scope of the present invention. It should be understood that the present invention is not limited to the specific embodiments described in the specification, except as defined in the appended claims.

What is claimed is:

1. A method of displaying a raised-resolution video of tissue inside a body at an increased frame rate in an ultrasonic diagnostic imaging system provided with a transducer for transmitting a ultrasonic wave pulse in response to a driving pulse while scanning the transmission direction in response to a scan control signal and for receiving an echo of the ultrasonic wave pulse to provide an echo signal, the method comprising the steps of:

supplying said driving pulses and said scan control signal to said transducer such that said transducer transmits weaker and stronger ultrasonic wave pulses alternately while putting the same intervals between adjacent ultrasonic wave pulses;

obtaining a weaker echo of said weaker ultrasonic wave pulse and a stronger echo of said stronger ultrasonic wave pulse from said transducer;

equalizing said weaker echo and a previous weaker echo obtained just before said weaker echo to said stronger echo into an equalized weaker echo and an equalized previous weaker echo, respectively;

calculating an interpolation value between said equalized weaker echo and said equalized previous weaker echo;

finding, for each weaker ultrasonic wave pulse, a value indicative of a difference between said interpolation value and a stronger echo obtained between said weaker echo and said previous weaker echo; and displaying a raised-resolution video of said tissue at an increased frame rate on the basis of said values and said scan control signal.

2. An ultrasonic diagnostic imaging system for displaying a raised-resolution video of tissue inside a body at an increased frame rate, the system comprising:

a transducer for transmitting a ultrasonic wave pulse in response to a driving pulse while scanning the transmission direction in response to a scan control signal and for receiving an echo of the ultrasonic wave pulse to provide an echo signal;

means for supplying said driving pulses and said scan control signal to said transducer such that said transducer transmits weaker and stronger ultrasonic wave pulses alternately while putting the same intervals between adjacent ultrasonic wave pulses to obtain a weaker echo of said weaker ultrasonic wave pulse and a stronger echo of said stronger ultrasonic wave pulse from said transducer;

means for equalizing each weaker echo to said stronger echo into an equalized weaker echo;

means for calculating an interpolation value between said equalized weaker echo and an equalized previous weaker echo obtained from a previous weaker echo;

means for finding, for each weaker ultrasonic wave pulse, a value indicative of a difference between said interpolation value and a stronger echo obtained between said weaker echo and said previous weaker echo; and means for displaying a raised-resolution video of said tissue at an increased frame rate on the basis of said values and said scan control signal.

3. A system as defined in claim 2, wherein said equalizing means comprises means for calculating a convolution by using each weaker echo as one of two components.

4. A system as defined in claim 2, wherein said means for supplying said driving pulses comprises means for supplying a narrower driving pulse and a wider driving pulse for said weaker and stronger ultrasonic wave pulses, respectively.

5. A system as defined in claim 2, wherein said means for supplying said driving pulses comprises means for supplying fewer driving pulse(s) for said weaker ultrasonic wave pulse and for supplying more driving pulses for said stronger ultrasonic wave pulse, all of said driving pulses having an identical width.

6. A system as defined in claim 4, wherein said equalizing means comprises means for calculating $ra(t)*invf(Pb(\omega)/Pa(\omega))$ for each weaker echo, where $ra(t)$ is a function of time $t$ which represents the weaker echo, $X*Y$ indicates a convolution of $X$ and $Y$, and $invf(Pb(\omega)/Pa(\omega))$ is an inverse Fourier transform of the function $Pb(\omega)/Pa(\omega)$, where $Pa(\omega)$ and $Pb(\omega)$ are Fourier transform of said narrower driving pulse $pa(t)$ and said wider driving pulse $pb(t)$.

7. A system as defined in claim 4, wherein said equalizing means comprises a digital filter for compensating a spectral difference between said narrower driving pulse and said wider driving pulse.

8. A system as defined in claim 2, wherein said calculating means comprises means for calculating an arithmetic means of said equalized weaker echo and said equalized previous weaker echo.

9. A system as defined in claim 2, wherein said calculating means comprises means for calculating an arithmetic means of the absolute values of said equalized weaker echo and said equalized previous weaker echo.

10. A system as defined in claim 2, wherein said means for finding a value comprises means for calculating said difference as said value.

11. A system as defined in claim 2, wherein said means for finding a value comprises means for calculating, as said value, a difference between the absolute values of said interpolation value and said stronger echo.

12. An ultrasonic diagnostic imaging system for displaying a raised-resolution video of tissue inside a body at an increased frame rate, the system comprising:

a transducer for transmitting a ultrasonic wave pulse in response to a driving pulse while scanning the transmission direction in response to a scan control signal and for receiving an echo of the ultrasonic wave pulse to provide an echo signal;

means for supplying said driving pulses and said scan control signal to said transducer such that said transducer transmits weaker and stronger ultrasonic wave pulses alternately while putting the same intervals between adjacent ultrasonic wave pulses to obtain a weaker echo of said weaker ultrasonic wave pulse and a stronger echo of said stronger ultrasonic wave pulse from said transducer;

means for equalizing each stronger echo to said weaker echo into an equalized stronger echo;

means for calculating an interpolation value between said equalized stronger echo and an equalized previous stronger echo obtained from a previous stronger echo;

means for finding, for each stronger ultrasonic wave pulse, a value indicative of a difference between said interpolation value and a weaker echo obtained between said stronger echo and said previous stronger echo; and means for displaying a raised-resolution video of said tissue at an increased frame rate on the basis of said values and said scan control signal.

\* \* \* \* \*